United States Patent [19]

Bruns, Jr. et al.

[11] Patent Number: 5,545,641

[45] Date of Patent: Aug. 13, 1996

[54] METHODS OF INHIBITING PHYSIOLOGICAL CONDITIONS ASSOCIATED WITH AN EXCESS OF BRADYKININ

[75] Inventors: Robert F. Bruns, Jr., Carmel; Donald R. Gehlert, Indianapolis, both of Ind.; J. Jeffry Howbert, Bellevue, Wash.; William H. W. Lunn, Indianapolis, Ind.

[73] Assignee: Eli Lilly and Company, Indianapolis, Ind.

[21] Appl. No.: 326,672

[22] Filed: Oct. 20, 1994

[51] Int. Cl.$^6$ .................................................. A61K 31/51
[52] U.S. Cl. ........................ 514/317; 514/319; 514/324
[58] Field of Search .................................. 514/317, 319, 514/324

[56] References Cited

U.S. PATENT DOCUMENTS

| | | |
|---|---|---|
| 4,133,814 | 1/1979 | Jones et al. . |
| 4,380,635 | 4/1983 | Peters . |
| 4,418,068 | 11/1983 | Jones . |

(List continued on next page.)

FOREIGN PATENT DOCUMENTS

| | | |
|---|---|---|
| WO93/10113 | 5/1993 | Japan . |
| WO93/1074 | 6/1993 | WIPO . |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene and Anti–Estrogen, Simulates the Effects of Estrogen in Inhibiting Bone Resorption Through Regulating TGFB–3 Expression in Bone;" .Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L. J. "Biological Actions and Binding Properties of a New Estrogen Antagosist LY117018," In: Homone Antagonists, 129–82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

(List continued on next page.)

Primary Examiner—Marianne M. Cintins
Assistant Examiner—Keith MacMillan
Attorney, Agent, or Firm—James J. Sales; David E. Boone

[57] ABSTRACT

A method of inhibiting a physiological condition associated with an excess of bradykinin comprising administering to a human in need thereof an effective amount of a compound having the formula

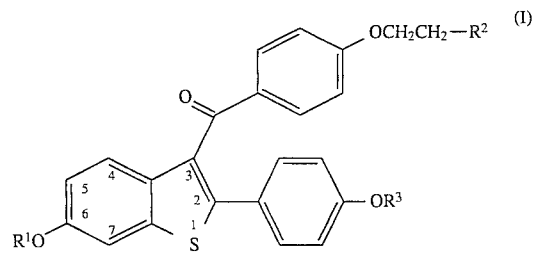

wherein $R^1$ and $R^3$ are independently hydrogen, —CH$_3$,

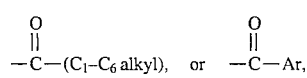

wherein Ar is optionally substituted phenyl;
$R^2$ is selected from the group consisting of pyrrolidine, hexamethyleneamino, and piperidino; or a pharmaceutically acceptable salt of solvate thereof.

4 Claims, No Drawings

U.S. PATENT DOCUMENTS

| | | | |
|---|---|---|---|
| 4,703,053 | 10/1987 | Connor et al. | 514/382 |
| 4,910,317 | 3/1990 | Connor et al. | 514/381 |
| 4,931,459 | 6/1990 | Connor et al. | 514/381 |
| 5,075,321 | 12/1991 | Schreiber | 514/317 |

OTHER PUBLICATIONS

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4,–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–HydroxyY–2–(4–hydroxyphenyl)benzol[b]thien–3–yl] [4–[2–(1–piperidinyl) ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Arg Pro Pro Gly Phe Ser Pro Phe Arg
    1                    5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Lys Arg Pro Pro Gly Phe Ser Pro Phe Arg
    1                    5                    1 0

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Met Lys Arg Pro Pro Gly Phe Ser Pro Phe Arg

METHODS OF INHIBITING PHYSIOLOGICAL CONDITIONS ASSOCIATED WITH AN EXCESS OF BRADYKININ

BACKGROUND OF THE INVENTION

Bradykinin is a nonapeptide having the amino acid sequence

Arg-Pro-Pro-Gly-Phe-Ser-Pro-Phe-Arg hereinafter referred to as SEQ ID NO:1, belonging to a family of kinins that also includes kallidin or lysyl-bradykinin which has the amino acid sequence Lys-Arg-Pro-Pro-Gly-Phe-Ser-Pro-Phe-Arg hereinafter referred to as SEQ ID NO:2, and methionyl-lysyl-bradykinin, which has the amino acid sequence Met-Lys-Arg-Pro-Pro-Gly-Phe-Ser-Pro-Phe-Arg hereinafter referred to as SEQ ID NO:3. These kinins are released from plasma precursors (kininogens) by the action of plasma and tissue kallikreins to regulate the essential physiological functions. [For a review of the therapeutic prospects of bradykinin receptor antagonists, see, J. N. Sharma, *General Pharmacology* 24:267–274 (1993).]

Bradykinin mediates pain, vascular permeability, inflammation, gastrointestinal function, and smooth muscle tone in vascular and other tissues. Bradykinin is one of the key mediators of the body's response to trauma and injury. Abnormally raised bradykinin release in response to noxious agents, tissue injury or lack of circulating kininases can induce several pathological conditions ranging from rheumatoid arthritis to asthma.

Receptors for bradykinin exist in the nervous system, epithelia, smooth muscle, and fibroblasts. In each tissue type bradykinin triggers specific responses including neurotransmitter release, muscle contraction, fluid secretion by epithelia, and stimulation of cell growth. The initial interaction for the biological response occurs at a bradykinin receptor site on a cell.

Bradykinin can activate neurons and produce neurotransmitter release. It can activate phospholipases C and $A_2$ resulting in the production of a number of bioactive intermediates.

Bradykinin receptors are G protein-coupled receptors that activate phospholipase C or phospholipase $A_2$ and increase the synthesis of inositol triphosphate, diacylglycerol, and arachidonic acid. Olsen, et al., *Journal of Bioloical Chemistry*, 263:18030–18035 (1988). G proteins are a family of membrane proteins that become activated only after binding guanosine triphosphate. Activated G proteins in turn activate an amplifier enzyme on the inner face of a membrane; the enzyme then converts precursor molecules into second messengers.

Bradykinin receptors have been classified as $B_1$ and $B_2$ on the basis of the relative potencies of agonists (kinins) and antagonists (kinin analogues) on various pharmacological preparations. R. J. Vavrek and J. M. Stewart, *Peptides*, 6:161–164 (1985). $B_1$ receptors are generated de novo in the vascular smooth muscle during incubation of isolated tissue and during antigen-induced arthritis. J. Bouthiller, et al., *British Journal of Pharmacology*, 92:257–264 (1987).

There continues to exist a need for non-peptidyl bradykinin receptor antagonists. Pharmacological agents containing guanidine moieties are known. See, e.g., U.S. Pat. Nos. 5,059,624 and 5,028,613. These two issued patents describe a series of pyrroloquinoline alkaloids isolated and purified from certain marine sponges. U.S. Pat. No. 5,288,725, issued Feb. 22, 1994, describes a series of pyrroloquinoline guanidine compounds useful as bradykinin receptor antagonists. U.S. Pat. No. 5,212,182, issued May 18, 1993, describes a series of quinolinyl- and naphthalenylbenzamides and benzylamines which are useful as bradykinin receptor antagonists possessing analgesic properties. U.S. Pat. No. 5,216,165, issued Jun. 1, 1993, describes a series of N-substituted aminoquinolines useful as analgesic agents by means of their properties as bradykinin receptor antagonists.

There continues to exist a need for efficacious and safe compounds which are useful as bradykinin receptor antagonists. The current invention provides a novel series of such antagonists which are administrable by a variety of routes, including orally as well as parenterally.

SUMMARY OF THE INVENTION

This invention provides a method of inhibiting a physiological disorder associated with an excess of bradykinin which comprises administering to a human in need thereof a therapeutically effective amount of a compound of Formula I

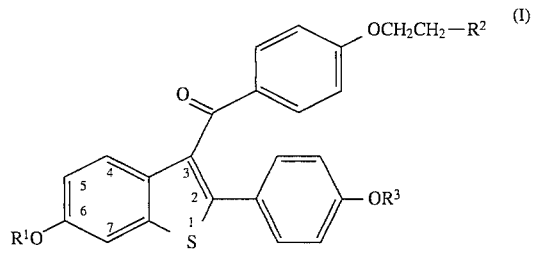

wherein $R^1$ and $R^3$ are independently hydrogen, —CH$_3$,

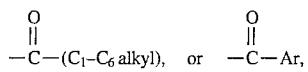

wherein Ar is optionally substituted phenyl;

$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting a physiological condition associated with an excess of bradykinin.

The therapeutic and prophylactic treatments provided by this invention are practiced by administering to a human in need thereof a dose of a compound of formula I or a pharmaceutically acceptable salt or solvate thereof, that is effective to inhibit a physiological condition associated with an excess of bradykinin, or its symptoms.

The term "inhibit" includes its generally accepted meaning which includes prohibiting, preventing, restraining, and slowing, stopping or reversing progression, severity or a resultant symptom. As such, the present method includes both medical therapeutic and/or prophylactic administration, as appropriate.

Raloxifene is a preferred compound of this invention and it is the hydrochloride salt of a compound of formula 1 wherein $R^1$ and $R^3$ are hydrogen and $R^2$ is 1-piperidinyl.

Generally, at least one compound of formula I is formulated with codon excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. The term "optionally substituted phenyl" includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by refernce.

The particular dosage of a compound of formula I required to inhibit a physiological condition associated with an excess of bradykinin, or its symptoms, according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively treat or prevent the disease(s) or symptom(s).

It is usually preferred to administer a compound of formula I in the form of an acid addition salt, as is customary in the administration of pharmaceuticals bearing a basic group, such as the piperidino ring. For such purposes the following oral dosage forms are available.

FORMULATIONS

In the formulations which follow, "Active ingredient" means a compound of formula I.

Formulation 1: Gelatin Capsules
Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

| Ingredient | Quantity (mg/capsule) |
| --- | --- |
| Formulation 2: Raloxifene capsule | |
| Raloxifene | 1 |
| Starch, NF | 112 |
| Starch flowable powder | 225.3 |
| Silicone fluid 350 centistokes | 1.7 |
| Formulation 3: Raloxifene capsule | |
| Raloxifene | 5 |
| Starch, NF | 108 |
| Starch flowable powder | 225.3 |
| Silicone fluid 350 centistokes | 1.7 |
| Formulation 4: Raloxifene capsule | |
| Raloxifene | 10 |
| Starch, NF | 103 |
| Starch flowable powder | 225.3 |
| Silicone fluid 350 centistokes | 1.7 |
| Formulation 5: Raloxifene capsule | |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The biological activity of the compounds of the present invention was evaluated employing an initial screening assay which rapidly and accurately measured the binding of the tested compound to known bradykinin receptor sites. Assays useful for evaluating bradykinin receptor antagonists are well known in the art. See, e.g., U.S. Pat. Nos. 5,162,497, issued Nov. 10, 1992; 5,212,182, issued May 18, 1993; 5,216,165, issued Jun. 1, 1993; and 5,288,725, issued Feb. 22, 1994, all of which are herein incorporated by reference. See also, Ransom, et al., *Biochemical Pharmacology*, 43:1823 (1992).

Guinea Pig Bradykinin Binding Assay

Guinea pigs were humanely sacrificed and the intestines were removed. These intestines were washed thoroughly with 0.9% saline, blotted dry and weighed. The tissues were homogenized in at least four volumes of 50 mM Tris buffer, pH 7.7, and centifuged at 15,000 g for about thirty minutes.

The pellets were then washed three times by successive suspensions in 50 mM Tris, pH 7.7, followed by centifugation. The final pellets were resuspended in a sufficient volume of 50 mM Tris, pH 7.7 to provide a concentration of 1 g of wet weight of tissue per 4 ml of buffer. These samples were stored frozen at −80° C.

For the binding assay 190–195 µl of assay buffer [50 mM Tris, pH 7.4, 1 mM 1,10-phenanthroline, and 10 µM Plummer's inhibitor] was admixed with 200 μl of tissue homogenate, and 5–10 μl of test sample, the additions occurring in the order listed. This assay mixture was then mixed throughly. Non-specific binding was determined in the presence of 1 μM unlabeled bradykinin.

To this assay cocktail was added 100 μl (1 nM) $^3$H-labeled bradykinin. The binding reaction was then incubated for about 90 minutes at room temperature and then filtered through GF/B glass fiber filters, the filters having been presoaked for at least one hour in 0.3% polyethyleneimine. The filters were washed with cold 50 mM Tris, pH 7.7 (3×3 ml) and then counted on a scintillation counter.

Many of the compounds prepared supra showed significant activity as bradykinin receptor antagonists. As the compounds of Formula I are effective bradykinin receptor antagonists, these compounds are of value in the treatment of a wide variety of clinical conditions which are characterized by the presence of an excess of bradykinin. Thus, the invention provides methods for the treatment or prevention of a physiological disorder associated with an excess of bradykinins, which method comprises administering to a mammal in need of said treatment an effective amount of a compound of Formula I or a pharmaceutically acceptable salt, solvate or prodrug thereof. The term "physiological disorder associated with an excess of bradykinins" encompasses those disorders associated with an inappropriate stimulation of bradykinin receptors, regardless of the actual amount of bradykinin present in the locale.

These physiological disorders may include disorders such as rhinitis, asthma, irritable bowel syndrome, ulcerative colitis, pain or nociception, inflammation, periodontitis, rheumatoid arthritis, and osteomyelitis. Bradykinins are also known to have important roles in circulation homeostasis and bradykinin receptor antagonists may, therefore, be useful in blood pressure regulation and the treatment or prevention of hypertension or hypotension. Bradykinin receptor antagonists are also useful in the treatment or prevention of endotoxic shock which results from an interaction of endotoxin produced from bacterial cell walls with cells of the reticuloendothelial system.

---

We claim:

1. A method of inhibiting a physiological condition associated with an excess of bradykinin comprising administering to a human in need thereof an effective amount of a compound having the formula

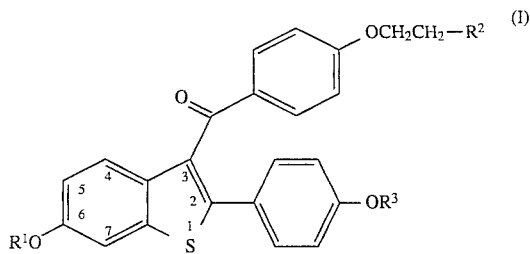

wherein $R^1$ and $R^3$ are independently hydrogen, $-CH_3$,

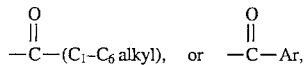

wherein Ar is optionally substituted phenyl;
$R^2$ is selected from the group consisting of pyrrolidino, hexamethyleneimino, and piperidino; or a pharmaceutically acceptable salt of solvate thereof, wherein said condition is pain or nociception, rhinitis, or asthma.

2. The method of claim 1 wherein said compound is the hydrochloride salt thereof.

3. The method of claim 1 wherein said administration is prophylactic.

4. The method of claim 1 wherein said compound

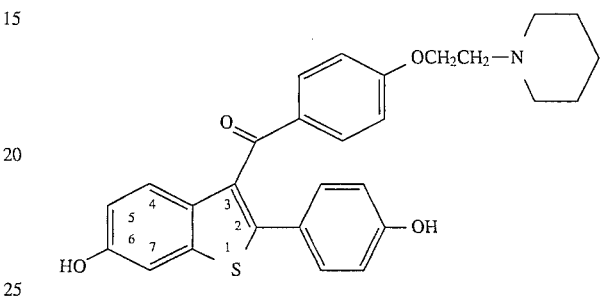

or its hydrochloride salt.

* * * * *